Figure 1:
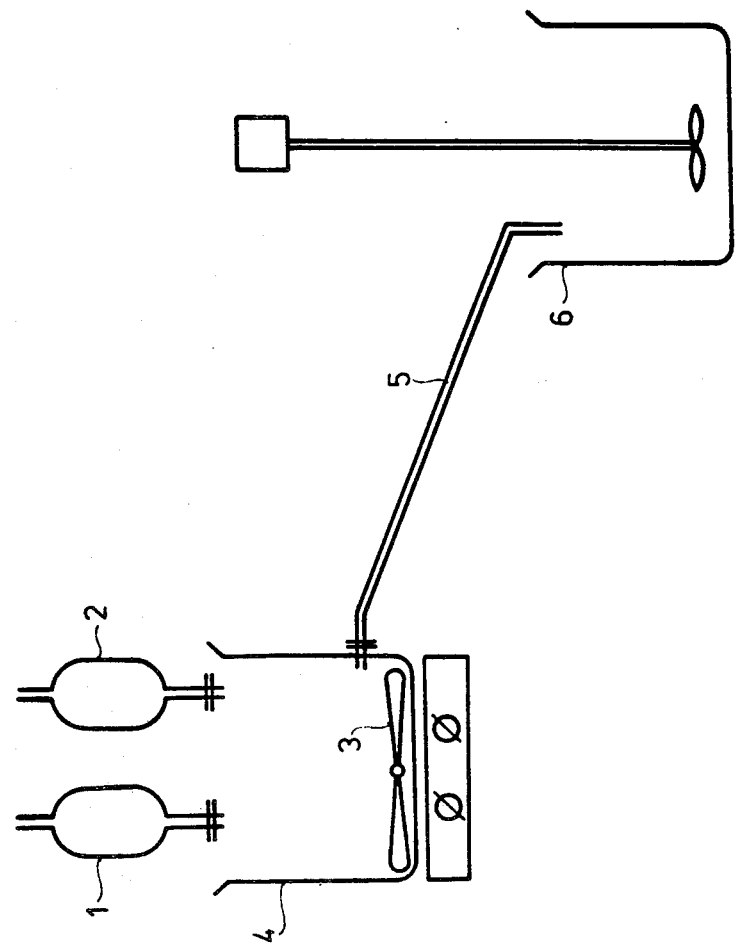

United States Patent [19]

Riedl et al.

[11] 4,396,630

[45] Aug. 2, 1983

[54] PROCESS FOR PREPARING LIPOID-BIOLOGICALLY ACTIVE PARTICLES

[75] Inventors: Zoltán Riedl, Budapest; László Sztankov, Szentendre; István Horváth, Budapest, all of Hungary

[73] Assignee: Human Oltoanyagtermelo es Kutato Intezet, Budapest, Hungary

[21] Appl. No.: 218,126

[22] Filed: Dec. 19, 1980

[30] Foreign Application Priority Data

Dec. 27, 1979 [HU] Hungary .............................. HU 299

[51] Int. Cl.³ .................. A61K 47/00; A61K 31/685; A61K 9/50; G01N 33/54
[52] U.S. Cl. ........................................ 424/365; 424/9; 424/1; 424/38; 424/85; 424/88; 424/89; 424/92; 424/199; 424/359; 436/829; 427/213.3
[58] Field of Search .......... 424/1, 2, 8, 9, 36, 424/38, 85, 88, 89, 92, 101, 177, 199, 359, 365; 252/316; 436/829

[56] References Cited

U.S. PATENT DOCUMENTS 3,265,629 8/1966 Jensen ..................................... 424/2

FOREIGN PATENT DOCUMENTS 51-26213 4/1976 Japan ................................... 424/38

OTHER PUBLICATIONS van Rooljen, Acta Histochem, vol. 65, 1979, pp. 41–48.
Tyrrell, Biochim. Biophys. Acta, vol. 457, 1976, pp. 263–277.
Hansen, The Amer. J. Tropical Med. & Hyg., vol. 25, 1976, pp. 422–426.
Gregoriadis, Eur. J. Biochem., vol. 47, 1974, pp. 179–185.

Primary Examiner—Anna P. Fagelson
Attorney, Agent, or Firm—Murray Schaffer

[57] ABSTRACT

Adjuvant particles are prepared from lipoid-soluble substances, and compositions comprising the particles and biologically active substances adsorbed thereon are provided. The adjuvant systems are capable of binding a wide variety of biologically active substances, and can be used in vivo and in vitro as well.

5 Claims, 1 Drawing Figure

PROCESS FOR PREPARING LIPOID-BIOLOGICALLY ACTIVE PARTICLES

This invention relates to particles prepared from lipoid-soluble substances, compositions comprising said particles and biologically active substances adsorbed thereon, as well as to a process for the preparation thereof.

According to the current techniques, in vitro tests are generally carried out with biologically active substances bound to a latex carrier (Am. J. Med. 21, 888–892/1956/). The latex carrier is a specially polymerized polystyrene suspension comprising polystyrene particles of appropriate size. It is well known that styrene, which is the starting material of this latex suspension, is highly subject to autopolymerisation. Therefore, from the commercially available styrene, the styrene monomer is separated by distillation and the monomer obtained is subjected to polymerization. In spite of this precaution, the suspension "ages" during storage, and, when the particles reach a given size, the reactant becomes unsuitable for carrying out precipitation reactions (J.A.M.A., 168 /2/, 180–181/1958/). This is most probably due to the fact that the latex suspension prepared from styrene also is liable to autopolymerisation.

The reactants containing a latex carrier are prepared in at least two steps. In the first step the carrier is prepared, on which the biologically active substances are adsorbed in a second step. This procedure is rather cumbersome and the reactants obtained can be used for in vitro tests only, since styrene is highly detrimental to the living organism.

For in vivo tests Freund adjuvants (Molecular Biology, 13 Biochemistry and Biophysics, 1973, New York) are widely used. Their use, however, even under experimental conditions, is strongly limited by side-effects, which render their application for human therapy impossible. In the human therapy metal-containing adjuvants (Molecular Biology, 13 Biochemistry and Biophysics, 1973 New York) and saponine-type immunostimulants, which have an influence on the blood picture (Acta vet. scand. 19, 7-40/1978/) are frequently used.

Recently it was attempted to use liposome for binding biologically active substances prior to parenteral administration (Proc. Nad. Acat. Sci. 72,88–92/1975/). Liposome is a particle formed from cholesterol and a non-heterogenous surface active agent. The particles are formed by admixing a solution of the two components in chloroform and adding a suitable agent to form the bonds, such as phosphatidyl choline. The chloroform phase is then distilled to dryness. In this way a lipid layer is formed on the wall of the container. Thereafter an aqueous solution of the biologically active substance is added to the film formed (British Patent Specification 28 131/74). It can be seen that the preparation is a step-by-step method, and, in one step, only a very small amount of the product can be obtained. The grain size of the particles prepared by this method varies widely.

The present invention provides a new carrier system, which does not have the disadvantages of the above listed adjuvants and which can be used in vivo and in vitro, respectively.

The carrier according to the invention is not liable to autopolymerization, is compatible with the living organism and therefore is equally suitable for in vivo and in vitro application. It can be used in various branches of immunology and biology including human and veterinary therapy.

It is naturally essential that the particles of the carrier should be capable of adsorbing the molecules of biologically active substances. A further requirement is that the formation of the particles and binding of the biologically active substances should be carried out in a single step, and the product should be obtained in large quantities economically.

It has surprisingly been found that the preparation of the carrier particles and the binding of the biologically active substances can be carried out in a single reaction step, when for example cholesterol and a non-heterogenous surface active agent e.g. egg lecithin are dissolved in alcohol; the biologically active substances, for example a bacterium, virus, cell fractions of bacteria or metabolites or derivatives thereof, various hormones, heptenes, having a poor immunogen activity per se or antibiotics are dissolved in an aqueous electrolyte system; the alcoholic and aqueous phases are combined.

Alternatively, the preparation can be carried out also in two steps. In this case the particle forming substances are dissolved in the alcoholic phase and the electrolyte phase is added to give so called "empty" particles. These particles are capable of binding biologically active substances.

The suspension obtained by either of the two methods described above is subjected to centrifugation; the precipitate is suspended in water or in an aqueous electrolyte solution and is subjected to an ultrasound treatment. The product is stored in a lyophilized or cooled form. The lyophilized product is sterilized by irradiation.

The carrier particles prepared from lipoid-soluble substances and the compositions comprising such particles and biologically active substances adsorbed thereon are also within the scope of the invention. These compositions are prepared by a new method, which comprises admixing a solution of a lipoid-soluble substance and a suitable surface active agent in alcohol or another suitable organic solvent (a) with a solution of a biologically active substance in water or an aqueous electrolyte solution having a pH-value of 2 to 10, in a volume ratio of 1:1000 to 9:1, stirring the reaction mixture for at least one minute, allowing it to stand for at most 7 days and separating the precipitated particles in a manner known per se; or (b) with water or an aqueous electrolyte solution, in a volume ratio of 1:1000 to 9:1, separating the particles precipitated and optionally suspending them in water or an aqueous electrolyte solution have a pH of 2 to 10 or lyophilizing same; or (c) with water or an aqueous electrolyte solution, in a volume ratio of 1:1000 to 9:1, separating the precipitated particles, adding said particles to a biologically active substance in water or in an aqueous electrolyte solution, stirring the solution for at least one minute and separating the particles formed in a manner known per se; or (d) adding to the particles prepared according to variant (b) a biologically active substance in water or an aqueous electrolyte solution having a pH of 2 to 10 and forming a suspension; and optionally lyophilizing and if desired sterilizing the product obtained by any one of process variants (a) or (c).

The most important advantages of the invention can be summarized as follows:

1. By the process according to the invention the preparation of the particles and binding of the biologically active substances, if desired, can be carried out in a single reaction step.

2. The process according to the invention can continuously be carried out, and allows the large scale preparation of the particles.

3. The particles are formed from substances which are compatible with the living organism.

4. The process is economical.

5. By the instant process new systems are available which can be used for quick immunodiagnostical examinations in vitro, e.g., a quick, quantitative determination of Rheumatoid arthritis; other reactants for rapid immunodiagnostical examinations can be prepared in a large variety.

6. An important advantage of the immunodiagnostical reactants referred to under point 5 above consists in the fact that the reaction can be carried out as a drop test and the result can be evaluated in a few minutes.

7. Since the particles of the carrier do not contain substances incompatible with the living organism, they are suitable for introducing the adsorbed biologically active substances into the living organism; and (a) in the case of active immunization with a virus, they are capable of increasing the antigenity of living, inactivated and disintegrated viruses as well;

(b) in the case of active immunization with a bacterium, they are capable of stimulating the immunization with inactivated, disintegrated bacteria, bacterium fractions and metabolites of bacteria;

(c) in the case of immunization with fungal fractions, they exert a considerable stimulating activity.

8. Biologically active substances, which induce a very small immune response in the living organism, can be absorbed by the particles prepared according to the invention, and in this way the immune response induced by them can considerably be increased. Thus, the particle system according to the invention is suitable for inducing an adjuvant effect (e.g. using haptens, hormones, enzymes, histamine). An important advantage of a parenteral injection carried out with the particles according to the invention consists in the fact that the injection does not induce any undesirable change either at the site of injection or in any other part of the organism. The substance is entirely adsorbed and has no side effect.

9. By the process according to the invention also biologically active substances, which are relatively rapidly eliminated from the living organism due to their small molecules (e.g. antibiotics, various chemotherapeutics, etc.), can be adsorbed, and in this way their elimination can considerably be slowed down, which results in a "prolonged effect".

Further details of the invention are to be found in the following examples, which are, however, not intended to limit the invention in any way. When carrying out the process the alcoholic or organic phase is admixed with the aqueous phase in a volume ratio of 1:1000–9:1. In this way an optimum amount of particles having an optimum size is obtained, and thus the adsorbing capacity of the particles for biologically active substances is ideal.

Process variant (a)

Both containers of the apparatus illustrated in FIG. 1 are filled up. Into container 1 a solution of lecithin and cholesterol in absolute ethanol is poured. Into container 2 an aqueous electrolyte solution containing the biologically active substance is poured. After starting stirrer 3, the content of the containers 1 and 2 is poured, dropped or sprayed into stirring container 4. After stirring at 50 r.p.m. for 1 minute, the suspension is transferred from the mixing container 4 through relief tube 5 into collector 6. In the collector 6, stirring is continued until a desired amount of particle suspension is obtained. The substance is incubated at 37° C. for 5 to 10 minutes. Thereafter the suspension is centrifuged at a speed of 6000 r.p.m. for 30 minutes. If a direct use is intended, the precipitate is taken up in a physiological saline solution, is carefully homogenized and subjected to an ultrasound treatment. If the preparation is to be stored, the precipitate obtained is taken up in distilled water, is carefully homogenized, and is lyophilized. The lyophilized product is sterilized by irradiation.

Process variant (b)

Both containers of the apparatus illustrated in FIG. 1 are filled up. Into the container 1, a solution of lecithin and cholesterol in absolute ethanol is poured. Into the container 2, an aqueous electrolyte solution is poured. After starting the stirrer 3, the contents of containers 1 and 2 are poured, dropped or sprayed into the stirring container 4. After stirring, the suspension is transferred from the mixing container 4 through relief tube 5 into the collector 6. In the collector 6, stirring is continued until a desired amount of particle suspension is obtained.

The suspension is centrifuged at a speed of about 6000 r.p.m. (4000–6000 g) for 30 minutes, whereupon it is decanted. The precipitate is taken up in distilled water, is carefully homogenized, subjected to an ultrasound treatment, and is lyophilized and sterilized by irradiation. A unit of an "empty" particle prepared by this process in a lyophilized form contains 11.2 mg. of dry substance, which corresponds to a particle number of 1.5 to $2.5 \times 10^8$.

Process variant (c)

Both containers of the apparatus shown in FIG. 1 are filled up. Into container 1, a solution of lecithin and cholesterol in absolute ethanol is added. Into the container 2, an aqueous electrolyte solution is poured. After starting the stirrer 3, the contents of the containers 1 and 2 are poured, dropped or sprayed into the mixing container 4. After stirring, the suspension is transferred from the container 4 through the relief tube 5 into the collector 6. In the collector 6, stirring is continued until a desired amount of particle suspension is obtained.

The suspension is centrifugal at a speed of about 6000 r.p.m. for 30 minutes, whereupon it is decanted. If a direct use is intended, the desired biologically active compound is taken up in a physiological saline solution and the precipitate obtained is suspended in this solution, whereupon it is homogenized and subjected to ultrasound treatment. If the precipitate is to be stored, the biologically active compound, previously taken up in water or in an aqueous electrolyte solution having a pH of 2 to 10 is added to the precipitate obtained, the mixture is carefully homogenized, subjected to ultrasound treatment, incubated at 37° C. for 5 to 10 minutes, and lyophilized.

Process variant (d)

The particles prepared according to process variant (b) can be used as an adjuvant in combination with optional biologically active compounds.

EXAMPLE 1

Production of hepatitis antibody

Living and inactivated hepatitis viruses are adsorbed by the particles by adding $10^9$ virus particles to one lyophilized particle unit, prepared according to the process variant (b). By the immune substance obtained, a higher antibody level can be achieved than known in the art.

EXAMPLE 2

Protecting effect by inactivated myxomatosis virus vaccine

Up to now, only vaccines prepared by living viruses provided protection against this virus. Rabbits were injected with an inactivated myxomatosis virus vaccine containing $10^6$ virus particles/ml. The rabbits were injected with 1 ml. of vaccine adsorbed on 1 particle unit prepared according to process variant (b), subcutaneously. Thirty days after the injection, the evaluated results showed that the vaccine prepared and used in this way showed a full protection even against a living virus representing 100 infective doses during the control experiments. If the particle unit is prepared according to process variant (a), the antibody level gives full protection against 10 infective doses.

EXAMPLE 3

Immunity against treponematoses

From disintegrated cells of the strain treponema pallidum Budapest ($10^7$/ml.), antigen is prepared by an ultrasound treatment; and the antigen obtained is bound to two units of lyophilized particles prepared according to process variant (b). Animals are injected once a week, altogether six times, using 1 ml. of antigen content, using intramuscular, intravenous and subcutaneous injections. In the animals treated in this way, a high specific antibody level and canker immunity are detected.

EXAMPLE 4

Immunity against tetanus (a) To a unit amount of particles prepared according to process variant (b), a unit amount of tetanus toxoid is added. The substance is lyophilized. Before use, the substance is suspended in a physiological saline solution corresponding to its original volume. The activity is tested according to the methods disclosed in the British Pharmacopoeia, United States Pharmacopoeia and Pharmacopeae Hungaricae VI on guinea pigs. It is clearly established that the immunogenic properties of the substance against tetanus are essentially better than the immuno-effect required in the prescriptions.

Tests were carried out also with a vaccine prepared according to process variant (a) and process variant (c), respectively. The results were the same as above described.

(b) To a unit amount of particles prepared according to process variant (b) various amounts of tetanus toxoid are bound. The substance is lyophilized, whereupon it is taken up in a physiological saline solution corresponding to the volume prior to lyophilization. The activity is tested on guinea pigs as described above. The specific antigenicity is better than prescribed, and in conformity with the dose-response law.

(c) To various amounts of particles prepared according to process variant (b), the same amount of tetanus toxoid is added. After lyophilization, the substance obtained is taken up in a physiological saline solution corresponding to the volume prior to lyophilization. The tests carried out on guinea pigs as described above clearly show that the antigenicity is better than prescribed in each case.

EXAMPLE 3

Immunization with combined bacterial antigens

To a unit amount of particles prepared according to process variant (b), a combination of tetanus, diphtheria and bacterial antigens is bound. After lyophilization, the substance is resuspended into its original volume and the activity of the antigen components is tested on guinea pigs and white mice, respectively, by the methods of Pharmacopoeia referred to in Example 4. The antigenic activity is the same or higher than prescribed.

EXAMPLE 6

The preparation of anti-choriogonadotropin (HCG) Immunoserum

For the preparation of antihormones, model tests are carried out with human choriogonadotropin (HCG). This traditionally poor immunogenic substance is connventionally adjuvated with an oily Freund adjuvant. 3000 E/mg. of HCG are bound to 1 particle unit, which has been prepared according to process variant (b). Using the vaccine prepared in this way, NZW rabbits weighing 2.5 kg. each are injected subcutaneously every two weeks. After the 7th injection, the anti-HCG antibody level surpasses the antibody level measured in the control group. Thereafter, the control group is injected by the same amount of HCG stimulated with a Freund adjuvant. Undesired side effects are observed in the control group contrary to the animals treated with the particles according to the invention, where no side effect appears. After this long immunizing period, the rabbits are drained of blood and are subjected to autopsy. The microscopic and histological examination of liver, kidney and lung shows no pathological change.

EXAMPLE 7

Preparation of antihistamine serum 2.7 mg. of detoxicated histamine (p-amino-benzenazo-histamine) are adsorbed on 2 particle units of a lyophilized carrier prepared according to process variant (b). Using the substance obtained, rabbits are injected every second day. After the 20th injection, a high level of antihistamine antibody is detected.

EXAMPLE 8

Preparation of gamma-globulin reactant bound to particles formed from lipoid-solutle substances (Process variant (a))

2 lit. of a 0.25% solution of gamma-globulin in a buffer having a pH of 6 are prepared. Simultaneously a solution of lipoid-soluble substances in absolute alcohol is prepared, which contains 0.01 to 0.6% egg lecithin and 0.1 to 2% cholesterol. The solutions are admixed as described in process variant (a).

The precipitate obtained is taken up in a physiological electrolyte solution (5 lit.) conventionally used for diluting blood serum, mixed, and subjected to ultrasound treatment to give a ready for use reactant.

EXAMPLE 9

The use of a gamma-globulin reactant bound to particles formed from lipoid-soluble substances for quantitative determination of rheumatoid factor Rheumatoid arthritis is accompanied by the presence of immune complexes, which react with normal human immunoglobulins. Their detection and the diagnosis of rheumatoid arthritis are actually based on this reaction, which is made visible for example by using latex particles or the very sensitive WAALER-ROSE reaction.

The properties of the latex adjuvant system have can be observed in one minute, and negative if no agglutination takes place in one minute.

The results of the test are listed in the following Table 1.

TABLE 1

| | Titre of lipoid particles bound to gamma-globulin Titre of WAALER-ROSE reaction (WRT) | | | | | | |
|---|---|---|---|---|---|---|---|
| Serum dilution | 0 | 32 | 64 | 128 | 256 | 512 | 1024 |
| concentrated | ± | ++++ | ++++ | ++++ | ++++ | ++++ | ++++ |
| 2 | − | +++ | ++++ | ++++ | ++++ | ++++ | ++++ |
| 4 | − | + | ++ | +++ | ++++ | ++++ | ++++ |
| 8 | − | ± | + | ++ | +++ | ++++ | ++++ |
| 16 | − | − | ± | + | +++ | +++ | ++++ |
| 32 | − | − | − | ± | ++ | +++ | +++ |
| 64 | − | − | − | − | ± | + | +++ |
| 128 | − | − | − | − | − | ± | ± | already been described in the introductory part of the specification.

The WAALER-ROSE reaction is a passive hemagglutinational method, which is rather cumbersome and its performance takes a long time.

The blood serums collected from the patients to be examined are heated at 56° C. for 30 minutes and are stored at +4° C. until use. If possible, fresh serums are used, but serums not older than one week can still be employed.

The serum to be examined is diluted with a physiological saline solution. One drop (0.05 ml.) is applied to a glass plate and, to the drops corresponding to different dilutions, 0.01 ml. portions of the reactant containing gamma-globulin (Example 8) are added.

The progress of the reaction is monitored after adding the reactant to the serum. The reactant should naturally be added to the diluted serum drops as soon as possible; the drops are carefully stirred with a glass stick, and the homogeneous admixture of the two substances is promoted by continuous agitation. The progress of the reaction is visually evaluated. The result is "0" if, in a given period of time, e.g. 5 minutes, no agglutination takes place. The grade of agglutination is illustrated by "crosses". Thus the grade of the reaction is marked by "++++" if strong aggregates are formed during the test period and the liquid between the precipitate clogs is cleared. The evaluation is facilitated by a magnifying glass. As a control, 1 drop of physiological saline solution used for the dilution of the serum and 0.01 ml. of the reactant are used. In the control, no agglutination takes place during the test period (5 minutes).

The formation of micro-aggregates can be monitored also by microscopic observation. In such cases, the reaction is carried out on the microscopic slide, and for reading 40 x objective and 7 x ocular are used.

The tests can be carried out also with concentrated, undiluted serums. The test is positive if agglutination

We claim:

1. Process for the preparation of particles from lipoid-soluble substances and compositions containing said particles and biologically active substances bound to them, which comprises admixing an egg lecithin and cholesterol dissolved in absolute alcohol, with (a) a biologically active substance taken up in an aqueous electrolyte having a pH of 2 to 10, in a volume ratio of 1:1000–9:1, stirring the reaction mixture for at least one minute, allowing it to stand for at most 7 days and separating the particles precipitated from the solution; or (b) an aqueous electrolyte having a pH of 2 to 10, in a volume ratio of 1:1000 to 9:1, and isolating the precipitated particles (c) an aqueous electrolyte solution in a volume ratio of 1:1000 to 9:1, isolating the precipitated particles, adding them to a biologically active substance taken up in an aqueous electrolyte solution having a pH of 2 to 10, stirring the solution obtained for at least two minutes, allowing to stand for at most 7 days and isolating the particles formed, or (d) adding to the particles prepared according to variant (b) a biologically active substance taken up in an aqueous electrolyte solution having a pH of 2 to 10 and forming a suspension.

2. A process as claimed in claim 1, which comprises separating the particles by centrifugation.

3. A process as claimed in claim 1, which comprises lyophilizing and sterilizing by irradiation the product prepared by variant (a).

4. A process as claimed in claim 1, which comprises lyophilizing and sterilizing by irradiation the product prepared by variant (c).

5. A process as claimed in claim 1, which comprises lyophilizing and sterilizing by irradiation the product prepared by variant (b).

* * * * *